US00PP19901P2

(12) United States Plant Patent
Westhoff

(10) Patent No.: US PP19,901 P2
(45) Date of Patent: Apr. 14, 2009

(54) ***VERBENA* PLANT NAMED 'WESVERCAVIO'**

(50) Latin Name: *Verbena hybrida*
Varietal Denomination: Wesvercavio

(75) Inventor: Heinrich Westhoff, Südlohn (DE)

(73) Assignee: J. + H. Westhoff Interpel, Südlohn (DE)

( * ) Notice: Subject to any disclaimer, the term of this patent is extended or adjusted under 35 U.S.C. 154(b) by 181 days.

(21) Appl. No.: 11/731,876

(22) Filed: Mar. 30, 2007

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent L Bell
*Assistant Examiner*—S. B. McCormick-Ewoldt
(74) *Attorney, Agent, or Firm*—C. A. Whealy

(57) ABSTRACT

A new and distinct cultivar of *Verbena* plant named 'Wesvercavio', characterized by its compact, mounding and cascading plant habit; vigorous growth habit; short internodes and freely branching habit; dense and bushy plant form; freely flowering habit; and intense purple violet to violet-colored flowers that are held above and beyond the foliage in mounded umbels.

1 Drawing Sheet

Botanical designation: *Verbena hydrida.*
cultivar denomination: 'Wesvercavio'.

BACKGROUND OF THE INVENTION

The present invention relates to a new and distinct cultivar of *Verbena,* botanically known as *Verbena hybrida,* and hereinafter referred to by the name 'Wesvercavio'.

The new *Verbena* is a product of planned breeding program conducted by the Inventor in Südlohn, Germany. The objective of the breeding program is to create new vigorous *Verbena* cultivars with early and freely flowering habits.

The new *Verbena* originated from a cross-pollination made by the Inventor in 2003 in Südlohn, Germany of a proprietary seedling selection of *Verbena hybrida* identified as code number 03P516, not patented, as the female, or seed, parent with a proprietary seedling selection of *Verbena hybrida* identified as code number 03P702, not patented, as the male, or pollen parent. The new *Verbena* was discovered and selected by the Inventor as a single flowering plant within the progeny of the stated cross-pollination in a controlled environment in Südlohn, Germany.

Asexual reproduction of the new *Verbena* by terminal cuttings in a controlled environment in Südlohn, Germany since 2004 has shown that the unique features of this new *Verbena* are stable and reproduced true to type in successive generations.

SUMMARY OF THE INVENTION

The cultivar Wesvercavio has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Wesvercavio'. These characteristics in combination distinguish 'Wesvercavio' as a new and distinct cultivar of *Verbena*:

1. Compact, mounding and cascading plant habit.
2. Vigorous growth habit.

3. Short internodes and freely branching habit; dense and bushy plant form.
4. Freely flowering habit.
5. Intense purple violet to violet-colored flowers that are held above and beyond the foliage in mounded umbels.

Plants of the new *Verbena* can be compared to plants of the female parent selection. Plants of the new *Verbena* differ from plants of the female parent selection in the following characteristics:

1. Plants of the new *Verbena* are more compact than plants of the female parent selection.
2. Inflorescences of plants of the new *Verbena* are more compact than and not as open and loose as inflorescences of plants of the female parent selection.
3. Flowers of plants of the new *Verbena* are fragrant whereas flowers of plants of the female parent selection are not fragrant.

Plants of the new *Verbena* can be compared to plants of the male parent selection. Plants of the new *Verbena* differ from plants of the male parent selection in the following characteristics:

1. Plants of the new *Verbena* have longer leaves than plants of the male parent selection.
2. Plants of the new *Verbena* have inflorescences positioned all over whereas plants of the male parent selection have flowers positioned only at the top of the plant.
3. Flowers of plants of the new *Verbena* are fragrant whereas flowers of plants of the male parent selection are not fragrant.

Plants of the new *Verbena* can be compared to plants of the *Verbena* cultivar USBENAS10, disclosed in U.S. Plant Pat. No. 15,673. In side-by-side comparisons conducted in S üdlohn, Germany, plants of the new *Verbena* differed from plants of the cultivar USBENAS10 in the following characteristics:

1. Plants of the new *Verbena* were more compact and had shorter internodes than plants of the cultivar USBENAS10.
2. Plants of the new *Verbena* were more freely branching than plants of the cultivar USBENAS10.

3. Plants of the new *Verbena* had shorter internodes than plants of the cultivar USBENAS10.
4. Plants of the new *Verbena* had longer leaves than plants of the cultivar USBENAS10.
5. Plants of the new *Verbena* and the cultivar USBENAS10 differed in flower color.
6. Flowers of plants of the new *Verbena* were fragrant whereas flowers of plants of the cultivar USBENAS10 were not fragrant.

BRIEF DESCRIPTION OF THE PHOTOGRAPHS

The accompanying colored photographs illustrate the overall appearance of the new *Verbena,* showing the colors as true as it is reasonably possible to obtain colored reproductions of this type. Colors in the photographs may differ slightly from the color values cited in the detailed botanical description which accurately describe the colors of the new *Verbena.*

The photograph at the top of the sheet comprises a side perspective view of a typical flowering plant of 'Wesvercavio' grown in a container.

The photograph at the bottom of the sheet is a close-up view of a typical inflorescence of 'Wesvercavio'.

DETAILED BOTANICAL DESCRIPTION

The aforementioned photographs and following observations, measurements and values describe plants grown in Südlohn, Germany in a glass-covered greenhouse during the spring and summer and under conditions which closely approximate commercial production. During the production of the plants, day temperatures ranged from 20° C. to 25° C., night temperatures ranged from 16° C. to 18° C. and light levels ranged from 3,000 to 50,000 lux. Plants were pinched one time and were about 30 weeks old when the photographs and the description were taken. In the description, color references are made to The Royal Horticultural Society Colour Chart, 1995 Edition, except where general terms of ordinary dictionary significance are used.

Botanical classification: *Verbena hybrida* cultivar Wesvercavio.

Parentage:

*Female, or seed, parent.*—Proprietary seedling selection of *Verbena hybrida* identified as code number 03P516, not patented.

*Male, or pollen, parent.*—Proprietary seedling selection of *Verbena hybrida* identified as code number 03P702, not patented.

Propagation:

*Type.*—Terminal cuttings.

*Time to initiate roots.*—About 10 to 14 days at 18° C.

*Time to produce a rooted cutting.*—About 21 to 23 days at 18° C.

*Root description.*—Fine, fibrous; white in color.

*Rooting habit.*—Freely branching.

Plant description:

*Plant habit.*—Initially upright, then mounding to cascading plant habit; compact growth habit. Freely branching habit with two lateral branches potentially forming at every node; pinching enhances lateral branch development; dense and bushy plant habit. Vigorous growth habit.

*Plant height.*—About 13 cm to 18 cm.

*Plant diameter.*—About 50 cm to 60 cm.

Lateral branch description:

*Length.*—About 24 cm to 30 cm.

*Diameter.*—About 2.4 mm.

*Internode length.*—About 1.6 cm.

*Texture.*—Densely pubescent.

*Color.*—144A.

Foliage description:

*Arrangement.*—Opposite, simple; sessile.

*Length.*—About 3.1 cm to 4.1 cm.

*Width.*—About 2 cm to 2.8 cm.

*Shape.*—Deeply dissected; doubly pinnatifid.

*Apex.*—Acute.

*Base.*—Attenuate.

*Margin.*—Deeply dissected.

*Texture, upper and lower surfaces.*—Densely pubescent; leathery.

*Venation pattern.*—Pinnate.

*Color.*—Developing foliage, upper surface: 137B. Developing foliage, lower surface: 137C. Fully expanded foliage, upper surface: 147A; venation, 147A. Fully expanded foliage, lower surface: 147B; venation, 147C.

Flower description:

*Flower arrangement and habit.*—Salverform flowers arranged in hemispherical terminal umbels; umbels dense and mounding; numerous umbels covering the entire plant. Flowers face upward or outward. Freely flowering habit with about 35 flowers per inflorescence.

*Natural flowering season.*—Plants flower continuously from the spring through the fall in Germany.

*Flower longevity.*—Flowers last about two weeks on the plant. Flowers not persistent.

*Fragrance.*—Clove-like.

*Inflorescence size.*—Diameter: About 3.6 cm to 3.9 cm. Height: About 2.3 cm to 2.5 cm.

*Flowers.*—Appearance: Flared trumpet, corolla fused, five-parted. Length: About 1.6 cm. Diameter: About 1.8 cm. Tube length: About 1.5 cm. Throat diameter: About 2.3 mm. Tube diameter, base: About 1.2 mm.

*Flower buds.*—Length: About 9 mm. Diameter: About 2 mm. Shape: Oblong. Color: 83A; towards the base, 138A to 138B.

*Corolla.*—Arrangement: Single whorl of five fused petals. Petal lobe length: About 8 mm. Petal lobe width: About 8 mm. Petal lobe shape: Roughly broadly cordate. Petal lobe apex: Emarginate to cordate. Petal margin: Entire. Petal texture, upper and lower surfaces: Smooth, glabrous; velvety. Color: Petal, when opening, upper surface: 83A. Petal, when opening, lower surface: N81A to N81B. Petal, fully opened, upper surface: N81A; color becoming closer to 83A with development. Petal, fully opened, lower surface: 81C. Throat: 77A to 77D. Tube; 77B to 77D.

*Calyx.*—Arrangement: Star-shaped calyx with five fused sepals. Sepal length: About 8.7 mm. Sepal width: About 1.8 mm. Sepal shape: Lanceolate. Sepal apex: Acute. Sepal margin: Serrate. Sepal texture, upper and lower surfaces: Pubescent; velvety; viscid. Sepal color, upper surface: 138A. Sepal color, lower surface: 138A to 138B.

*Peduncles.*—Length: About 2.8 cm. Diameter: About 1 mm. Strength: Strong; wiry. Texture: Pubescent. Color: 144A.

*Pedicels.*—Flowers are sessile.

*Reproductive organs.*—Stamens: Quantity/arrangement: Four per flower, adnate to corolla tube.

Filament length: About 1 mm. Filament color: 145D. Anther shape: Two-parted; ovate. Anther length: About 1 mm. Anther diameter: Less than 1 mm. Anther color: 144C. Pollen amount: Scarce. Pollen color: 145C. Pistils: Quantity: One per flower. Pistil length: About 1.1 cm. Stigma shape: Ovate. Stigma color: 144A. Style length: About 9 mm. Style color: 145D. Ovary color: 144A. Fruits/seed: Fruit and seed development have not been observed.

Temperature tolerance: Plants of the new *Verbena* have been observed to tolerate temperatures from about 4° C. to about 30° C.

Pathogen/pest resistance: Plants of the new *Verbena* have not been observed to be resistant to pathogens and pests common to *Verbenas*.

It is claimed:

1. A new and distinct *Verbena* plant named 'Wesvercavio' as illustrated and described.

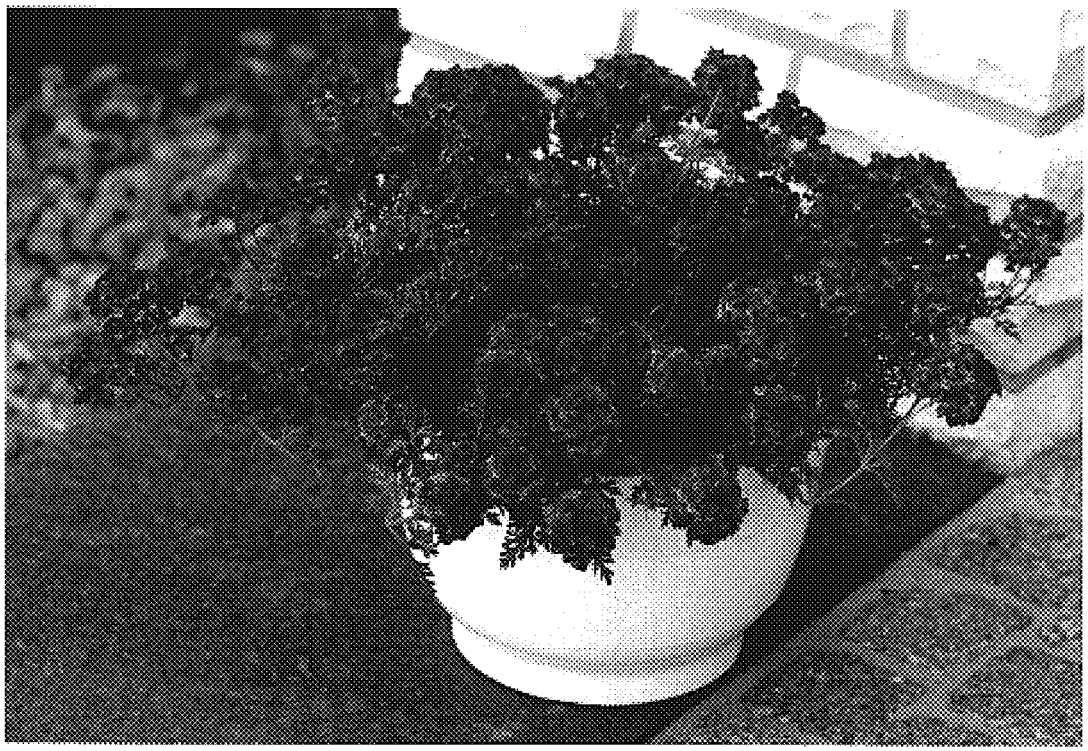
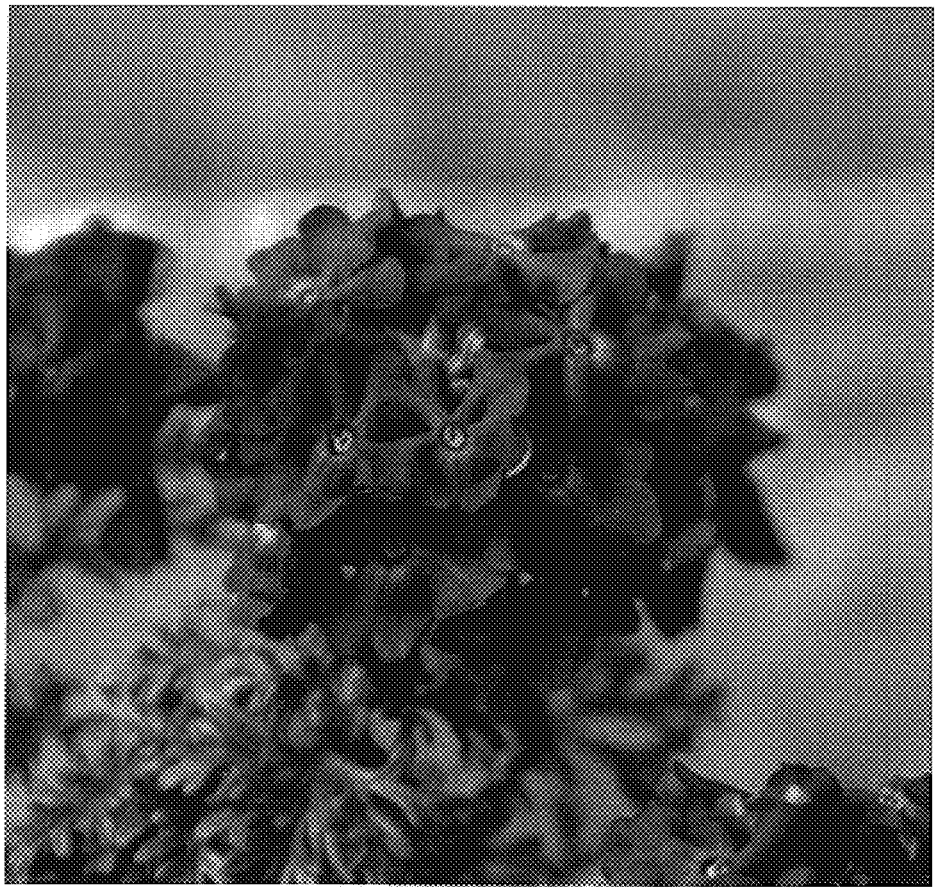

* * * * *